United States Patent [19]

Watanabe et al.

[11] Patent Number: 5,349,092
[45] Date of Patent: Sep. 20, 1994

[54] PROCESS FOR PRODUCING CATALYSTS FOR SYNTHESIS OF UNSATURATED ALDEHYDES AND UNSATURATED CARBOXYLIC ACIDS

[75] Inventors: Seigo Watanabe, Otake; Motomu Oh-Kita, Tokyo, both of Japan

[73] Assignee: Mitsubishi Rayon Co., Ltd., Tokyo, Japan

[21] Appl. No.: 22,648

[22] Filed: Feb. 25, 1993

[30] Foreign Application Priority Data

Feb. 27, 1992 [JP] Japan .................. 4-076076

[51] Int. Cl.$^5$ .................. C07C 45/34; B01J 27/28
[52] U.S. Cl. .................. 568/480; 502/34; 502/211
[58] Field of Search .................. 568/476, 479, 480; 502/34, 211

[56] References Cited

U.S. PATENT DOCUMENTS

| | | | |
|---|---|---|---|
| 4,190,608 | 2/1980 | Grasselli | 568/480 |
| 4,267,386 | 5/1981 | Vanderspurt | 568/480 |
| 4,306,090 | 12/1981 | Kirch et al. | 568/480 |
| 4,321,160 | 3/1982 | Farrington | 252/437 |
| 4,471,061 | 9/1984 | Shaw et al. | |
| 4,471,062 | 9/1984 | Farrington et al. | |

FOREIGN PATENT DOCUMENTS

| | | |
|---|---|---|
| 0058046A1 | 8/1982 | European Pat. Off. . |
| 0223877A1 | 6/1987 | European Pat. Off. . |
| 0267556A2 | 5/1988 | European Pat. Off. . |
| 0293859 | 12/1988 | European Pat. Off. . |
| 0460932A2 | 12/1991 | European Pat. Off. . |
| 3338380A1 | 4/1984 | Fed. Rep. of Germany . |
| 2917890A1 | 12/1990 | Fed. Rep. of Germany . |
| 56-91846 | 7/1981 | Japan . |
| 57-130949 | 8/1982 | Japan . |
| 58-121236 | 7/1983 | Japan . |
| 59-31727 | 2/1984 | Japan . |
| 60-28824 | 2/1985 | Japan . |
| 63-66141 | 3/1988 | Japan . |

*Primary Examiner*—Werren B. Lone
*Attorney, Agent, or Firm*—Armstrong, Westerman, Hattori, McLeland & Naughton

[57] ABSTRACT

Disclosed is a process for producing a multicomponent catalyst containing molybdenum and bismuth and used for synthesis of unsaturated aldehydes and unsaturated carboxylic acids, characterized in that dried starting materials for the catalyst are calcinated in an atmosphere containing 1 vol % or more of a nitrogen oxide and 0.5 vol % or more of oxygen.

1 Claim, No Drawings

PROCESS FOR PRODUCING CATALYSTS FOR SYNTHESIS OF UNSATURATED ALDEHYDES AND UNSATURATED CARBOXYLIC ACIDS

BACKGROUND OF THE INVENTION

The present invention relates to a process for producing catalysts for synthesis of unsaturated aldehydes and unsaturated carboxylic acids, namely, catalysts used for synthesis of acrolein and acrylic acid or methacrolein and methacrylic acid by gas phase catalytic oxidation of propylene, isobutylene or tertiary butanol with molecular oxygen.

Hitherto, many processes have been proposed for production of catalysts used for synthesis of unsaturated aldehydes and unsaturated carboxylic acids. In the case of using isobutylene or tertiary butanol as a starting material, many catalysts used for preparation of methacrolein and methacrylic acid by gas phase catalytic oxidation of isobutylene or tertiary butanol at high temperatures are proposed, for example, in Japanese Patent Kokai (Laid-Open) Nos.57-130949, 58-121236, 59-31727, 60-28824 and 63-66141. However, most of these proposals concern with the kinds of the elements which constitute the catalysts and the ratios of the elements. Some of them disclose processes of calcinating a catalyst precursor at a temperature within a specific range in the course of preparation of the catalyst, but none of them refer to calcinate the precursor in an atmosphere of a specific gas composition. Besides, the catalysts obtained by these processes have not yet reached the sufficient level as industrial catalysts. Further improvements are demanded from the industrial view point of catalyst performances such as catalytic activity and selectivity for the desired products.

SUMMARY OF THE INVENTION

An object of the present invention is to provide a process for producing a novel catalyst for advantageous synthesis of acrolein and acrylic acid or methacrolein and methacrylic acid from propylene, isobutylene or tertiary butanol.

The present invention relates to a process for producing a multicomponent catalyst containing molybdenum and bismuth and used for synthesis of unsaturated aldehydes and unsaturated carboxylic acids which comprises drying a mixed solution or an aqueous slurry containing at least a molybdenum compound and a bismuth compound as components and calcinating the resulting dry product wherein the dry product is calcinated in an atmosphere containing 1 vol % or more of a nitrogen oxide and 0.5 vol % or more of oxygen for at least 2 minutes in the calcination stage carried out at a temperature in the range of 200°–600° C.

DETAILED DESCRIPTION OF PREFERRED EMBODIMENTS

The starting materials for the elements which are catalyst components containing molybdenum and bismuth are unlimited in the present invention, but generally are oxides or chlorides, sulfates, nitrates, carbonates or ammonium salts capable of being converted to oxides by strong heating or mixtures thereof.

In the present invention there are no special limitations in the process of drying the mixed solution or aqueous slurry containing the catalyst components and in the state of the resulting dry products. For example, powdered dry products may be obtained by using an ordinary spray dryer, slurry dryer or drum dryer or block or flaky dry products may be obtained using an ordinary box dryer or tunnel dryer.

In the present invention there are no limitations in the types of calcination furnaces used for calcination of the dry products and in the method of calcination. For example, the dry products in fixed state may be calcinated using an ordinary box calcination furnace, tunnel calcination furnace or the like. Alternatively, the dry products in fluid state may be calcinated using a rotary kiln or the like.

The calcination temperature in the calcination stage is preferably in the range of 200°–600° C. When the calcination is carried out at a temperature outside the above range, catalysts having high performance cannot be sometimes obtained and this is not preferred. The time for which the calcination is continued after the temperature has reached a given level is not critical, but if the calcination time is too short, catalysts having high performance can be obtained with difficulty. Therefore, it is preferred to continue the calcination for 10 minutes or longer.

According to the present invention, the dry products are calcinated in an atmosphere containing 1 vol % or more of a nitrogen oxide and 0.5 vol % or more of oxygen for at least 2 minutes in the calcination stage, whereby catalysts which are able to give the objective products in a high yield can be obtained in a high reproducibility. The nitrogen oxide is preferably nitrogen dioxide or a mixture of several nitrogen oxides mainly composed of nitrogen dioxide. When the concentration of the nitrogen oxide in the calcination stage is lower than a prescribed value or when the time for which the concentration of the nitrogen oxide is maintained at a prescribed value or higher is too short, the effect to improve the catalyst performance tends to decrease and this is not preferred. Furthermore, when the calcination is carried out in an atmosphere containing no oxygen, the catalyst performance extremely deteriorates and this is not preferred.

The method for maintaining the concentration of the nitrogen oxide at a prescribed value or higher in the atmosphere in the calcination stage is unlimited, but relatively easy is a method of feeding the nitrogen oxide to the calcination furnace during calcination or a method of previously introducing into a calcination furnace a substance which produces a nitrogen oxide upon decomposition by heating, for example, nitric acid compounds such as nickel nitrate and ammonium nitrate or aqueous nitric acid solution. Furthermore, when nitrates such as bismuth nitrate are used as starting materials for the catalysts, nitrogen oxides, mainly nitrogen dioxide, are produced by calcination of the dry products in the calcination stage. In this case, the concentration of the nitrogen oxide can be maintained at a prescribed value or higher by retaining a certain amount of the produced nitrogen oxide in the calcination furnace without discharging it too much from the furnace. For example, the prescribed concentration can be maintained by controlling the amount of the air fed to the calcination furnace to less than a certain amount or by feeding no air to the furnace.

The timing at which the nitrogen oxide atmosphere is maintained in the calcination stage is not critical. However, as a result of the investigation, it has been found that it is especially preferred to maintain the nitrogen oxide atmosphere at the initial stage of the calcination, namely, about the time when the temperature of the dry product heated in the calcination furnace reaches 200°–300° C.

When acrolein and acrylic acid or methacrolein and methacrylic acid are produced by gas phase catalytic oxidation of propylene, isobutylene or tertiary butanol with molecular oxygen using the catalyst obtained by the process of the present invention, the molar ratio of propylene, isobutylene or tertiary butanol to oxygen is preferably 1:0.5–3. The starting material propylene, isobutylene or tertiary butanol is preferably diluted with an inert gas. The molecular oxygen used for oxidation may be pure oxygen, but use of air is industrially advantageous. The reaction pressure is from normal pressure to several atm. The reaction temperature is preferably in the range of 200°–450° C. The reaction can be carried out in either a fluidized bed or a fixed bed.

The effects of the present invention are illustrated by the following nonlimiting examples.

The "part" in the following examples and comparative examples means "part by weight". The analysis was conducted by gas chromatography. The concentration of the nitrogen oxides in the atmosphere was measured only on nitrogen dioxide. The reaction rate of propylene, isobutylene or tertiary butanol as a starting material and the selectivity of unsaturated aldehydes and unsaturated carboxylic acids are defined as follows:

Reaction rate of starting material (%) =

$$\frac{\text{Mol number of the reacted starting material}}{\text{Mol number of the fed starting material}} \times 100$$

Selectivity of unsaturated aldehyde =

$$\frac{\text{Mol number of the produced unsaturated aldehyde}}{\text{Mol number of the reacted starting material}} \times 100$$

Selectivity of unsaturated carboxylic acid =

$$\frac{\text{Mol number of the produced unsaturated carboxylic acid}}{\text{Mol number of the reacted starting material}} \times 100$$

EXAMPLE 1

To 1000 parts of water were added 500 parts of ammonium paramolybdate, 18.5 parts of ammonium paratungstate, 34.4 parts of antimony trioxide, 18.4 parts of cesium nitrate and 354.5 parts of 20% silica sol, followed by stirring under heating (solution A). Separately, 250 parts of 60% aqueous solution of nitric acid was added to 850 parts of water to obtain a homogeneous solution. Then, 57.2 parts of bismuth nitrate was dissolved therein. Then, 238.4 parts of ferric nitrate, 4.7 parts of chromium nitrate, 411.8 parts of nickel nitrate and 60.5 parts of magnesium nitrate were added in succession to the above prepared solution and dissolved therein (solution B). The solution B was added to the solution A to prepare a slurry. The slurry was dried by a spray dryer to obtain a powdered dry product.

The resulting dry product was introduced into a rotary kiln calcination furnace and calcinated at 500° C. The concentrations of nitrogen dioxide and oxygen in the atmosphere in the calcination furnace were measured after 10 minutes from the introduction of the dry product into the calcination furnace to obtain 45.4 vol % and 9.9 vol %, respectively. After lapse of further 10 minutes, the concentrations of nitrogen dioxide and oxygen were measured in the same manner to obtain 43.6 vol % and 10.3 vol %, respectively. The calcination was continued for additional 1 hour to obtain a catalyst powder.

The resulting catalyst had the composition represented by the following formula.

$$Mo_{12}W_{0.3}Bi_{0.5}Sb_1Fe_{2.5}Cr_{0.05}Si_5Ni_6Cs_{0.4}Mg_1O_x$$

(wherein Mo, W, Bi, Sb, Fe, Cr, Si, Ni, Cs, Mg and O denote molybdenum, tungsten, bismuth, antimony, iron, chromium, silicon, nickel, cesium, magnesium and oxygen, respectively, the numerals attached to the respective elemental symbols mean the atomic ratio of the respective elements, and x is the number of oxygen atoms necessary for satisfying the valences of the respective components).

The resulting catalyst was packed in a stainless steel reaction tube and a mixed starting material gas comprising 5% of isobutylene, 12% of oxygen, 10% of water vapor and 73% of nitrogen was passed through the catalyst bed with a contacting time of 3.6 seconds to carry out the reaction at 360° C. As a result, the reaction rate of isobutylene was 96.5%, the selectivity of methacrolein was 86.8% and the selectivity of methacrylic acid was 5.0%.

EXAMPLE 2

The reaction was carried out in the same manner as in Example 1 using the catalyst of Example 1 except that tertiary butanol was used as the starting material. As a result, the reaction rate of tertiary butanol was 100%, the selectivity of methacrolein was 86.1% and the selectivity of methacrylic acid was 3.3%.

COMPARATIVE EXAMPLE 1

A catalyst having the same composition as an Example 1 was prepared in the same manner as in Example 1 except for the calcination stage. That is, the calcination of the dry product at 500° C. using a rotary kiln calcination furnace was carried out with feeding the air to the calcination furnace. After lapse of 10 minutes from the initiation of the calcination, the concentrations of nitrogen dioxide and oxygen in the atmosphere in the calcination furnace were measured to obtain 0.6 vol % and 19.9 vol %, respectively. The nitrogen oxides in the atmosphere in the furnace at that time was analyzed to find that most of them was nitrogen dioxide.

The reaction was carried out in the same manner as in Example 1 using the thus obtained catalyst. The reaction rate of isobutylene was 94.4%, the selectivity of methacrolein was 86.5% and the selectivity of methacrylic acid was 4.8%. Thus, the catalyst obtained was lower in activity than the catalyst of Example 1.

EXAMPLE 3

A catalyst having the same composition as in Example 1 was prepared in the same manner as in Example 1 except for the calcination stage. That is, the calcination of the dry product at 500° C. in a rotary kiln calcination furnace was carried out with feeding the air to the calcination furnace for 15 minutes immediately after starting of the calcination and then, feeding of the air was discontinued for only 5 minutes, and thereafter, the calcination was carried out with feeding the air again. The concentrations of nitrogen dioxide and oxygen in the atmosphere in the calcination furnace after 10 minutes from starting of the calcination, namely, at the time when the air was being fed were measured to obtain 0.6 vol % and 19.9 vol %, respectively. Successively, after lapse of 18 minutes from the starting of the calcination, namely, at the time when the feeding of the air was discontinued, the concentrations of nitrogen dioxide and oxygen in the atmosphere in the calcination furnace were measured to obtain 24.9 vol % and 14.0 vol %, respectively. Subsequently, after lapse of 25 minutes from the starting of the calcination, namely, at the time when the feeding of the air was again being conducted, the concentrations of nitrogen dioxide and oxygen in the atmosphere in the calcination furnace were measured to obtain 0.5 vol % and 19.9 vol %, respectively.

The reaction was carried out in the same manner as in Example 1 using the above obtained catalyst. As a result, the reaction rate of isobutylene was 96.5%, the selectivity of methacrolein was 86.8% and the selectivity of methacrylic acid was 5.0%. That is, even when the time of maintaining the concentration of the nitrogen oxide at a prescribed value or higher in the calcination stage was shortened to 5 minutes, the resulting catalyst was equivalent to the catalyst of Example 1.

COMPARATIVE EXAMPLE 2

A catalyst having the same composition as in Example 1 was prepared in the same manner as in Example 1 except for the calcination stage. That is, the calcination of the dry product at 500° C. in a rotary kiln calcination furnace was carried out with feeding the air to the calcination furnace for 15 minutes immediately after starting of the calcination and then, feeding of the air was discontinued for only 1 minute, and thereafter, the calcination was carried out with feeding the air again. The concentrations of nitrogen dioxide and oxygen in the atmosphere of the calcination furnace after 10 minutes from starting of the calcination, namely, at the time when the air was being fed were measured to obtain 0.6 vol % and 19.9 vol %, respectively. Successively, after lapse of 15.5 minutes from the starting of the calcination, namely, at the time during which the feeding of the air was discontinued, the concentrations of nitrogen dioxide and oxygen in the atmosphere of the calcination furnace were measured to obtain 24.9 vol % and 4.0 vol %, respectively. Subsequently, after lapse of 20 minutes from the starting of the calcination, namely, at the time when the air was again being fed, the concentrations of nitrogen dioxide and oxygen in the atmosphere of the calcination furnace were measured to obtain 0.5 vol % and 19.9 vol %, respectively.

The reaction was carried out in the same manner as in Example 1 using the resulting catalyst. As a result, the reaction rate of isobutylene was 94.9%, the selectivity of methacrolein was 86.6% and the selectivity of methacrylic acid was 4.8%. That is, when the time of maintaining the concentration of the nitrogen oxide at a prescribed value or higher in the calcination stage was shortened to 1 minute, the resulting catalyst was lower in activity than the catalyst of Example 1.

EXAMPLE 4

500 parts of ammonium paramolybdate, 18.5 parts of ammonium paratungstate and 1.4 part of potassium nitrate were added to 1000 parts of water and stirred under heating. Then, thereto was added a solution prepared by dissolving 4.1 parts of 85% aqueous solution of phosphoric acid in 100 parts of water and further stirred under heating (solution A). Separately, 41.9 parts of 60% aqueous solution of nitric acid was added to 250 parts of water to obtain a homogeneous solution. Then, 114.5 parts of bismuth nitrate was dissolved therein. Then, thereto were added 95.3 parts of ferric nitrate, 309.0 parts of cobalt nitrate, 7.0 parts of zinc nitrate and 2.0 parts of silver nitrate in succession and 700 parts of water was further added thereto and well stirred (solution B). The solution B was added to the solution A to prepare a slurry and this slurry was heated to evaporate most of water. The resulting cake was dried at 120° C. to obtain a block-like dry product.

300 parts of the resulting block-like dry product was put in a stainless steel container and separately, 100 parts of nickel nitrate was put in a titanium container and both the containers were placed in a box-type calcination furnace. The dry product in the calcination furnace was heated to 520° C. from room temperature at a rate of 100° C./hr and successively calcinated by carrying out a heat treatment at that temperature for 2 hours. The concentrations of nitrogen dioxide and oxygen in the atmosphere of the calcination furnace when the temperature in the calcination furnace reached 250° C. were measured to obtain 12.1 vol % and 16.6 vol %, respectively. Furthermore, the concentrations of nitrogen dioxide and oxygen in the atmosphere of the calcination furnace when the temperature in the calcination furnace reached 300° C. were measured to obtain 10.7 vol % and 16.9 vol %, respectively.

The resulting catalyst had the composition represented by the following formula.

$Mo_{12}W_{0.3}Bi_1Fe_1P_{0.15}Ag_{0.05}Co_{4.5}K_{0.06}Zn_{0.1}O_x$ (wherein Mo, W, Bi, Fe, P, Ag, Co, K, Zn and O denote molybdenum, tungsten, bismuth, iron, phosphorus, silver, cobalt, potassium, zinc and oxygen, respectively, the numerals attached to the respective elemental symbols mean the atomic ratio of the respective elements, and x is the number of oxygen atoms necessary for satisfying the valences of the respective components).

The resulting catalyst was packed in a stainless steel reaction tube and a mixed starting material gas comprising 5% of propylene, 12% of oxygen, 10% of water vapor and 73% of nitrogen was passed through the catalyst bed for a contacting time of 3.6 seconds to carry out the reaction at 310° C. As a result, the reaction rate of propylene was 99.3%, the selectivity of acrolein was 90.2% and the selectivity of acrylic acid was 6.0%.

EXAMPLE 5

A catalyst having the same composition as in Example 4 was prepared in the same manner as in Example 4 except for the calcination stage. That is, the calcination of the dry product in the box-type calcination furnace was carried out with feeding a small amount of the air to the calcination furnace. The concentrations of nitrogen dioxide and oxygen in the atmosphere of the calcination furnace when the temperature in the calcination furnace reached 250° C. were measured to obtain 2.2 vol % and 19.6 vol %, respectively. The concentrations of nitrogen dioxide and oxygen in the atmosphere of the calcination furnace when the temperature in the calcination furnace reached 300° C. were measured to obtain 2.0 vol % and 19.6 vol %, respectively.

The reaction was carried out in the same manner as in Example 4 using the thus obtained catalyst. The reaction rate of propylene was 99.3%, the selectivity of acrolein was 90.2% and the selectivity of acrylic acid was 6.0%. Thus, the catalyst obtained was equivalent to the catalyst of Example 4.

COMPARATIVE EXAMPLE 3

A catalyst having the same composition as in Example 4 was prepared in the same manner as in Example 4 except for the calcination stage. That is, the calcination was carried out with feeding nitrogen to the calcination furnace. The concentrations of nitrogen dioxide and oxygen in the atmosphere of the calcination furnace when the temperature in the calcination furnace reached 250° C. were measured to obtain 11.9 vol % and 0 vol %, respectively.

The reaction was carried out in the same manner as in Example 4 using the thus obtained catalyst. The reaction rate of propylene was 85.1%, the selectivity of acrolein was 83.5% and the selectivity of acrylic acid was 3.9%. Thus, the catalyst obtained was very low in performance.

EXAMPLE 6

A catalyst having the same composition as in Example 4 was prepared in the same manner as in Example 4 except for the calcination stage. That is, the calcination of the dry product in the box-type calcination furnace was carried out with feeding a small amount of a mixed gas comprising 97 vol % of nitrogen and 3 vol % of oxygen to the calcination furnace. The concentrations of nitrogen dioxide and oxygen in the atmosphere of the calcination furnace when the temperature in the calcination furnace reached 250° C. were measured to obtain 10.4 vol % and 2.7 vol %, respectively. Furthermore, the concentrations of nitrogen dioxide and oxygen in the atmosphere of the calcination furnace when the temperature in the calcination furnace reached 300° C. were measured to obtain 10.0 vol % and 2.7 vol %, respectively.

The reaction was carried out in the same manner as in Example 4 using the thus obtained catalyst. The reaction rate of propylene was 99.3%, the selectively of reaction rate of propylene was 99.3%, the selectivity of acrolein was 90.2% and the selectivity of acrylic acid was 6.0%. Thus, the catalyst obtained was equivalent to the catalyst of Example 4.

COMPARATIVE EXAMPLE 4

A catalyst having the same composition as in Example 4 was prepared in the same manner as in Example 4 except for the calcination stage. That is, the calcination was carried out with feeding a small amount of a mixed gas comprising 99.8 vol % of nitrogen and 0.2 vol % of oxygen to the calcination furnace. The concentrations of nitrogen dioxide and oxygen in the atmosphere of the calcination furnace when the temperature in the calcination furnace reached 250° C. were measured to obtain 10.4 vol % and 0.2 vol %, respectively. Furthermore, the concentrations of nitrogen dioxide and oxygen in the atmosphere of the calcination furnace when the temperature in the calcination furnace reached 300° C. were measured to obtain 10.0 vol % and 0.2 vol %, respectively.

The reaction was carried out in the same manner as in Example 4 using the thus obtained catalyst. The reaction rate of propylene was 88.4%, the selectivity of acrolein was 89.8% and the selectivity of acrylic acid was 5.5%. Thus, the catalyst obtained was low in performance.

What is claimed is:

1. A process for preparing a molybdenum and bismuth containing catalyst for synthesizing meth(acrolein) and meth(acrylic) acid from propylene, isobutylene or tertiary butanol, which comprises drying a solution or a slurry containing a molybdenum compound and a bismuth compound to obtain a dried product, and calcining the dried product at 200°–600° C. for at least 2 minutes in atmosphere containing 1 vol % or more of a nitrogen oxide and 0.5 vol % or more of oxygen.

* * * * *